(12) United States Patent
Clayton

(10) Patent No.: US 8,307,830 B2
(45) Date of Patent: Nov. 13, 2012

(54) ENDOTRACHEAL CUFF AND TECHNIQUE FOR USING THE SAME

(75) Inventor: Jessica Clayton, Campbell, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1784 days.

(21) Appl. No.: 11/540,354

(22) Filed: Sep. 29, 2006

(65) Prior Publication Data

US 2008/0078403 A1  Apr. 3, 2008

(51) Int. Cl.
*A61M 16/00* (2006.01)
*A61M 29/00* (2006.01)
*A61M 31/00* (2006.01)
*A61F 2/06* (2006.01)

(52) U.S. Cl. ......... 128/207.15; 128/200.26; 128/207.14; 128/207.16; 604/101.02; 604/101.05; 604/103.05; 604/103.06; 604/103.11; 604/103.12; 604/103.13; 604/103.14; 604/500; 604/509; 606/191; 606/192; 606/193; 606/194; 623/1.11

(58) Field of Classification Search ............. 128/200.26, 128/207.14, 207.15, 207.16; 604/101.02, 604/500, 509, 101.05, 103.05, 103.06, 103.11, 604/103.12, 103.13, 103.14; 606/193, 191, 606/192, 194; 623/1.11
See application file for complete search history.

(56) References Cited

U.S. PATENT DOCUMENTS

| | | | |
|---|---|---|---|
| 2,927,584 A | 3/1960 | Wallace | |
| 3,769,983 A | 11/1973 | Merav | |
| 3,810,474 A | 5/1974 | Cross | |
| 3,822,238 A | 7/1974 | Blair et al. | |
| 3,913,565 A | 10/1975 | Kawahara | |
| 3,971,385 A | 7/1976 | Corbett | |
| 3,975,350 A | 8/1976 | Hudgin et al. | |
| 3,995,643 A | 12/1976 | Merav | |
| 4,022,217 A | 5/1977 | Rowean | |
| 4,130,617 A | 12/1978 | Wallace | |
| 4,230,108 A | 10/1980 | Young | |
| 4,231,365 A | 11/1980 | Scarberry | |
| 4,235,239 A | 11/1980 | Elam | |
| 4,328,056 A * | 5/1982 | Snooks | 156/242 |
| 4,340,046 A | 7/1982 | Cox | |
| 4,417,576 A | 11/1983 | Baran | |
| 4,495,948 A | 1/1985 | Shapiro | |
| 4,552,558 A | 11/1985 | Muto | |
| 4,569,344 A | 2/1986 | Palmer | |
| 4,638,539 A | 1/1987 | Palmer | |
| 4,649,913 A | 3/1987 | Watson | |

(Continued)

FOREIGN PATENT DOCUMENTS

CA    2353007    6/2000

(Continued)

OTHER PUBLICATIONS

International Search Report PCT/US2007/020543, 5 pages, mailed Nov. 27, 2008.

(Continued)

*Primary Examiner* — Patricia Bianco
*Assistant Examiner* — Nihir Patel

(57) ABSTRACT

A multi-layer inflatable balloon cuff may be adapted to seal a patient's trachea when associated with an endotracheal tube. The outer layer and the inner layer of the balloon cuff may have different material properties that may enhance a cuff's mechanical pressure seal by reducing wrinkles or folds that may form against a patient's tracheal walls.

50 Claims, 5 Drawing Sheets

U.S. PATENT DOCUMENTS

| | | | |
|---|---|---|---|
| 4,696,296 A | 9/1987 | Palmer | |
| 4,700,700 A | 10/1987 | Eliachar | |
| 4,791,920 A | 12/1988 | Fauza | |
| 4,791,923 A * | 12/1988 | Shapiro | 128/207.15 |
| 4,825,859 A | 5/1989 | Lambert | |
| 4,825,861 A | 5/1989 | Koss | |
| 4,834,726 A | 5/1989 | Lambert | |
| 4,836,199 A | 6/1989 | Palmer | |
| 4,838,255 A | 6/1989 | Lambert | |
| 4,840,173 A | 6/1989 | Porter | |
| 4,850,348 A | 7/1989 | Pell et al. | |
| 4,867,153 A | 9/1989 | Lorenzen et al. | |
| 4,872,579 A | 10/1989 | Palmer | |
| 4,886,059 A | 12/1989 | Weber | |
| 4,927,412 A | 5/1990 | Menasche | |
| 4,938,741 A | 7/1990 | Lambert | |
| 4,963,313 A | 10/1990 | Noddin et al. | |
| 4,967,743 A | 11/1990 | Lambert | |
| 4,979,505 A | 12/1990 | Cox | |
| 5,020,534 A | 6/1991 | Pell et al. | |
| 5,021,045 A | 6/1991 | Buckberg et al. | |
| 5,025,806 A | 6/1991 | Palmer et al. | |
| 5,029,580 A | 7/1991 | Radford et al. | |
| 5,033,466 A | 7/1991 | Weymuller, Jr. | |
| 5,060,646 A | 10/1991 | Page | |
| 5,065,754 A | 11/1991 | Jensen | |
| 5,074,840 A | 12/1991 | Yoon | |
| 5,076,268 A | 12/1991 | Weber | |
| 5,098,379 A | 3/1992 | Conway et al. | |
| 5,103,816 A | 4/1992 | Kirschbaum et al. | |
| 5,107,829 A | 4/1992 | Lambert | |
| 5,120,322 A | 6/1992 | Davis et al. | |
| 5,122,122 A | 6/1992 | Allgood | |
| 5,133,345 A | 7/1992 | Lambert | |
| 5,135,516 A | 8/1992 | Sahatjian et al. | |
| 5,137,671 A | 8/1992 | Conway et al. | |
| 5,158,569 A | 10/1992 | Strickland et al. | |
| 5,165,420 A | 11/1992 | Strickland | |
| 5,176,638 A | 1/1993 | Don Michael | |
| 5,190,810 A | 3/1993 | Kirschbaum et al. | |
| 5,199,427 A | 4/1993 | Strickland | |
| 5,201,310 A | 4/1993 | Turnbull et al. | |
| 5,207,643 A | 5/1993 | Davis | |
| 5,215,522 A | 6/1993 | Page et al. | |
| 5,218,957 A | 6/1993 | Strickland | |
| 5,230,332 A | 7/1993 | Strickland | |
| 5,233,979 A | 8/1993 | Strickland | |
| 5,246,012 A | 9/1993 | Strickland | |
| 5,250,070 A | 10/1993 | Parodi | |
| 5,251,619 A | 10/1993 | Lee | |
| 5,261,896 A | 11/1993 | Conway et al. | |
| 5,263,478 A | 11/1993 | Davis | |
| 5,269,770 A | 12/1993 | Conway et al. | |
| 5,277,177 A | 1/1994 | Page et al. | |
| 5,290,585 A | 3/1994 | Elton | |
| 5,304,121 A | 4/1994 | Sahatjian | |
| 5,331,027 A | 7/1994 | Whitbourne | |
| 5,360,402 A | 11/1994 | Conway et al. | |
| 5,370,656 A | 12/1994 | Shevel | |
| 5,370,899 A | 12/1994 | Conway et al. | |
| 5,374,261 A | 12/1994 | Yoon | |
| 5,392,774 A * | 2/1995 | Sato | 128/207.15 |
| 5,392,787 A | 2/1995 | Yoon | |
| 5,397,302 A | 3/1995 | Weaver et al. | |
| 5,407,423 A | 4/1995 | Yoon | |
| 5,417,671 A | 5/1995 | Jackson | |
| 5,423,745 A | 6/1995 | Todd et al. | |
| 5,439,457 A | 8/1995 | Yoon | |
| 5,443,063 A | 8/1995 | Greenberg | |
| 5,447,497 A * | 9/1995 | Sogard et al. | 604/101.02 |
| 5,447,505 A | 9/1995 | Valentine et al. | |
| 5,451,204 A | 9/1995 | Yoon | |
| 5,466,231 A | 11/1995 | Cercone et al. | |
| 5,469,864 A | 11/1995 | Rosenblatt | |
| 5,482,740 A | 1/1996 | Conway et al. | |
| 5,484,426 A | 1/1996 | Yoon | |
| 5,487,730 A | 1/1996 | Marcadis et al. | |
| 5,494,029 A | 2/1996 | Lane et al. | |
| 5,501,669 A | 3/1996 | Conway et al. | |
| 5,507,284 A | 4/1996 | Daneshvar | |
| 5,509,899 A | 4/1996 | Fan et al. | |
| 5,524,642 A | 6/1996 | Rosenblatt | |
| 5,545,132 A | 8/1996 | Fagan et al. | |
| 5,556,391 A | 9/1996 | Cercone et al. | |
| 5,593,718 A | 1/1997 | Conway et al. | |
| 5,599,292 A | 2/1997 | Yoon | |
| 5,599,299 A | 2/1997 | Weaver et al. | |
| 5,599,321 A | 2/1997 | Conway et al. | |
| 5,611,336 A | 3/1997 | Page et al. | |
| 5,613,950 A | 3/1997 | Yoon | |
| 5,649,902 A | 7/1997 | Yoon | |
| 5,653,229 A | 8/1997 | Greenberg | |
| 5,670,111 A | 9/1997 | Conway et al. | |
| 5,674,192 A | 10/1997 | Sahatjian et al. | |
| 5,693,014 A | 12/1997 | Abele et al. | |
| 5,694,922 A | 12/1997 | Palmer | |
| 5,697,365 A | 12/1997 | Pell | |
| 5,700,239 A | 12/1997 | Yoon | |
| 5,715,815 A | 2/1998 | Lorenzen et al. | |
| 5,720,726 A | 2/1998 | Marcadis et al. | |
| 5,722,931 A | 3/1998 | Heaven | |
| 5,730,123 A | 3/1998 | Lorenzen | |
| 5,733,252 A | 3/1998 | Yoon | |
| 5,735,271 A | 4/1998 | Lorenzen et al. | |
| 5,765,559 A | 6/1998 | Kim | |
| 5,769,882 A | 6/1998 | Fogarty et al. | |
| 5,810,786 A | 9/1998 | Jackson et al. | |
| 5,819,723 A | 10/1998 | Joseph | |
| 5,819,733 A | 10/1998 | Bertram | |
| 5,827,215 A | 10/1998 | Yoon | |
| 5,843,017 A | 12/1998 | Yoon | |
| 5,843,028 A | 12/1998 | Weaver et al. | |
| 5,843,060 A | 12/1998 | Cercone | |
| 5,843,089 A | 12/1998 | Sahatjian et al. | |
| 5,868,719 A | 2/1999 | Tsukernik | |
| 5,868,776 A * | 2/1999 | Wright | 606/194 |
| 5,908,406 A | 6/1999 | Ostapchenko | |
| 5,951,597 A | 9/1999 | Westlund et al. | |
| 5,954,706 A | 9/1999 | Sahatjian | |
| 5,954,740 A | 9/1999 | Ravenscroft et al. | |
| 5,971,954 A | 10/1999 | Conway et al. | |
| 5,976,072 A | 11/1999 | Greenberg | |
| 5,997,503 A | 12/1999 | Willis et al. | |
| 5,997,546 A | 12/1999 | Foster et al. | |
| 6,010,480 A | 1/2000 | Abele et al. | |
| 6,012,451 A | 1/2000 | Palmer | |
| 6,048,332 A | 4/2000 | Duffy et al. | |
| 6,110,192 A | 8/2000 | Ravenscroft et al. | |
| 6,129,547 A | 10/2000 | Cise | |
| 6,152,136 A | 11/2000 | Pagan | |
| 6,169,123 B1 | 1/2001 | Cercone | |
| 6,210,364 B1 | 4/2001 | Anderson et al. | |
| 6,214,895 B1 | 4/2001 | Cercone | |
| 6,227,200 B1 | 5/2001 | Crump et al. | |
| 6,240,321 B1 | 5/2001 | Janke et al. | |
| 6,248,088 B1 | 6/2001 | Yoon | |
| 6,264,631 B1 | 7/2001 | Willis et al. | |
| 6,264,633 B1 | 7/2001 | Knorig | |
| 6,277,089 B1 | 8/2001 | Yoon | |
| 6,312,421 B1 | 11/2001 | Boock | |
| 6,322,586 B1 | 11/2001 | Monroe et al. | |
| 6,364,856 B1 | 4/2002 | Ding et al. | |
| 6,378,521 B1 | 4/2002 | Van Den Berg | |
| 6,394,093 B1 | 5/2002 | Lethi | |
| 6,395,012 B1 | 5/2002 | Yoon et al. | |
| 6,398,266 B1 | 6/2002 | Crump | |
| 6,409,716 B1 | 6/2002 | Sahatjian et al. | |
| 6,481,436 B1 | 11/2002 | Neame | |
| 6,494,203 B1 | 12/2002 | Palmer | |
| 6,524,274 B1 | 2/2003 | Rosenthal et al. | |
| 6,526,977 B1 | 3/2003 | Göbel | |
| 6,543,451 B1 | 4/2003 | Crump et al. | |
| 6,551,272 B2 | 4/2003 | Gobel | |
| 6,572,813 B1 | 6/2003 | Zhang et al. | |
| 6,584,970 B1 | 7/2003 | Crump et al. | |
| 6,588,425 B2 | 7/2003 | Rouns et al. | |
| 6,588,427 B1 | 7/2003 | Carlsen et al. | |

| | | |
|---|---|---|
| 6,602,218 B2 | 8/2003 | Yoon |
| 6,602,219 B2 | 8/2003 | Madsen et al. |
| 6,609,520 B1 | 8/2003 | Carlsen et al. |
| 6,612,304 B1 | 9/2003 | Cise et al. |
| 6,612,305 B2 | 9/2003 | Fauza |
| 6,613,025 B1 | 9/2003 | Palasis |
| 6,615,835 B1 | 9/2003 | Cise et al. |
| 6,620,128 B1 | 9/2003 | Simhambhatla |
| 6,623,450 B1 | 9/2003 | Dutta |
| 6,629,530 B2 | 10/2003 | Cise |
| 6,632,091 B1 | 10/2003 | Cise et al. |
| 6,647,984 B1 | 11/2003 | O'Dea |
| 6,651,664 B1 | 11/2003 | Lomholt |
| 6,688,306 B1 | 2/2004 | Cise et al. |
| 6,698,424 B2 | 3/2004 | Madsen et al. |
| 6,705,320 B1 | 3/2004 | Anderson |
| 6,722,368 B1 | 4/2004 | Shaikh |
| 6,726,696 B1 | 4/2004 | Houser et al. |
| 6,732,734 B2 * | 5/2004 | Ogushi et al. ............ 128/207.15 |
| 6,745,773 B1 | 6/2004 | Gobel |
| 6,767,340 B2 | 7/2004 | Willis et al. |
| 6,769,430 B1 | 8/2004 | Carlsen et al. |
| 6,770,066 B1 | 8/2004 | Weaver et al. |
| 6,786,876 B2 | 9/2004 | Cox |
| 6,790,221 B2 | 9/2004 | Monroe et al. |
| 6,796,309 B2 | 9/2004 | Nash et al. |
| 6,802,317 B2 | 10/2004 | Göbel |
| 6,805,125 B1 | 10/2004 | Crump et al. |
| 6,808,521 B1 | 10/2004 | McMichael |
| 6,814,730 B2 | 11/2004 | Li |
| 6,890,339 B2 | 5/2005 | Sahatjian et al. |
| 6,908,449 B2 | 6/2005 | Willis et al. |
| 6,916,307 B2 | 7/2005 | Willis et al. |
| 6,923,786 B2 | 8/2005 | Rouns et al. |
| 6,997,909 B2 | 2/2006 | Goldberg |
| 7,040,321 B2 | 5/2006 | Gobel |
| 7,040,322 B2 | 5/2006 | Fortuna |
| 7,066,905 B2 | 6/2006 | Squire et al. |
| 7,147,352 B2 | 12/2006 | Teuscher et al. |
| 7,258,120 B2 | 8/2007 | Carlsen et al. |
| 7,360,540 B2 | 4/2008 | Brain et al. |
| 2002/0032407 A1 | 3/2002 | Willis et al. |
| 2002/0082552 A1 | 6/2002 | Ding et al. |
| 2002/0195110 A1 | 12/2002 | Watton |
| 2003/0116162 A1 | 6/2003 | Madsen et al. |
| 2003/0225369 A1 | 12/2003 | McMichael et al. |
| 2003/0225392 A1 | 12/2003 | McMichael et al. |
| 2003/0225393 A1 | 12/2003 | McMichael et al. |
| 2004/0079376 A1 | 4/2004 | Melker |
| 2004/0106899 A1 | 6/2004 | McMichael et al. |
| 2004/0106900 A1 | 6/2004 | Triebes et al. |
| 2004/0106901 A1 | 6/2004 | Letson et al. |
| 2004/0116898 A1 | 6/2004 | Hawk |
| 2004/0154623 A1 | 8/2004 | Schaeffer et al. |
| 2004/0193100 A1 | 9/2004 | Van Hooser et al. |
| 2004/0193101 A1 | 9/2004 | Van Hooser et al. |
| 2004/0215142 A1 | 10/2004 | Matheis et al. |
| 2004/0221853 A1 | 11/2004 | Miller |
| 2004/0255951 A1 | 12/2004 | Grey |
| 2005/0004560 A1 | 1/2005 | Cox |
| 2005/0033267 A1 | 2/2005 | Decaria |
| 2005/0033268 A1 | 2/2005 | Decaria |
| 2005/0033269 A1 | 2/2005 | Decaria |
| 2005/0038381 A1 | 2/2005 | McMichael |
| 2005/0065468 A1 | 3/2005 | Goebel |
| 2005/0124932 A1 | 6/2005 | Foster et al. |
| 2005/0124935 A1 | 6/2005 | McMichael |
| 2005/0137619 A1 | 6/2005 | Schewe et al. |
| 2005/0166924 A1 | 8/2005 | Thomas et al. |
| 2007/0163599 A1 | 7/2007 | Mijers |

FOREIGN PATENT DOCUMENTS

| | | |
|---|---|---|
| DE | 19500550 | 7/1996 |
| DE | 19855521 | 6/2000 |
| EP | 0214721 A1 | 3/1987 |
| EP | 0884061 | 6/1998 |
| EP | 1267981 | 4/2000 |
| EP | 1005877 | 6/2000 |
| EP | 1135184 | 6/2000 |
| GB | 1313347 A1 | 4/1973 |
| GB | 2168256 | 6/1986 |
| WO | WO 95/22367 | 8/1995 |
| WO | WO 00/27461 | 5/2000 |
| WO | WO 00/32262 | 6/2000 |
| WO | WO 00/32263 | 6/2000 |
| WO | WO 03/045487 | 6/2003 |
| WO | WO 2004/067262 | 8/2004 |
| WO | WO 2004/101046 | 11/2004 |
| WO | WO 2006/023486 | 3/2006 |
| WO | WO 2007140262 A1 | 12/2007 |
| WO | WO 2007149202 A1 | 12/2007 |
| WO | WO 2008042117 A1 | 4/2008 |

OTHER PUBLICATIONS

U.S. Appl. No. 11/472,733, filed Jun. 22, 2006, Nelson.
U.S. Appl. No. 11/472,915, filed Jun. 22, 2006, Morris et al.
U.S. Appl. No. 11/473,285, filed Jun. 22, 2006, Colburn et al.
U.S. Appl. No. 11/473,362, filed Jun. 22, 2006, Nelson.
U.S. Appl. No. 11/529,117, filed Sep. 28, 2006, Martens et al.
Dullenkopf, et al., "Fluid leakage past tracheal tube cuffs: evaluation on the new Microcuff endotracheal tube," *Intensive Care Medicine*, (2003) vol. 29, pp. 1849-1853.
Tecogel brochure page, Noveon Thermedics Polymer Products, Oct. 2003.
Ayşe Gönen Karakeçili et al.; "Comparison of Bacterial and Tissue Cell Initial Adhesion on Hydrophilic/Hydrophobic Biomaterials," J Biomater. Sci. Polymer Edn, vol. 13, No. 2, pp. 185-196 (2002).
Blunt et al.; "Gel Lubrication of the Tracheal Tube Cuff Reduces Pulmonary Aspiration," 2001 American Society of Anesthesiologists, Inc. Lippincott Williams & Wilkins, Inc.; Anesthesiology, V. 95, No. 2, Aug. 2001.
Shintani; "Modification of Medical Device Surface to Attain Anti-Infection," National Institute of Health Sciences; Trends Biomater. Artif. Organs, vol. 18(1), pp. 1-8 (2004).
Sartomer Application Bulletin; "Functional Acrylic Monomers as Modifiers for PVC Plastisol Formulations," pp. 1-6, Dec. 1997.

* cited by examiner

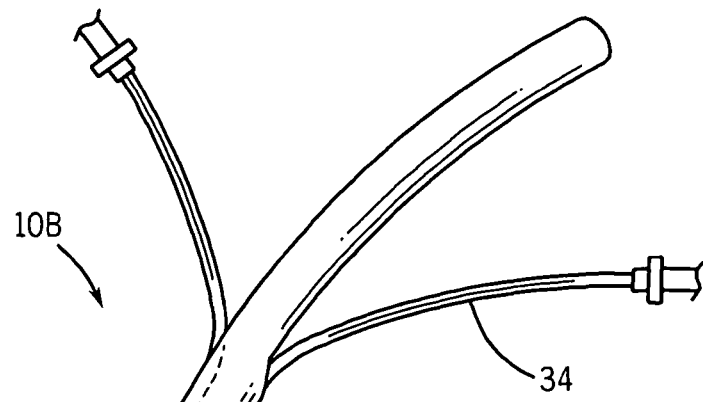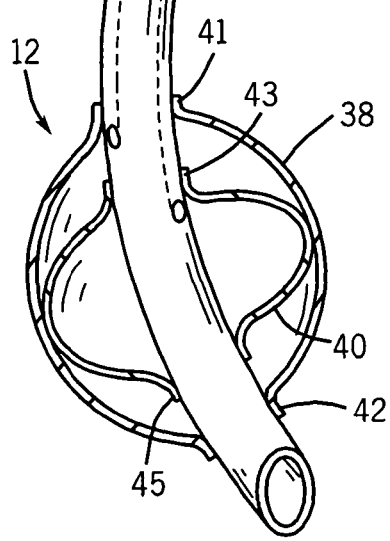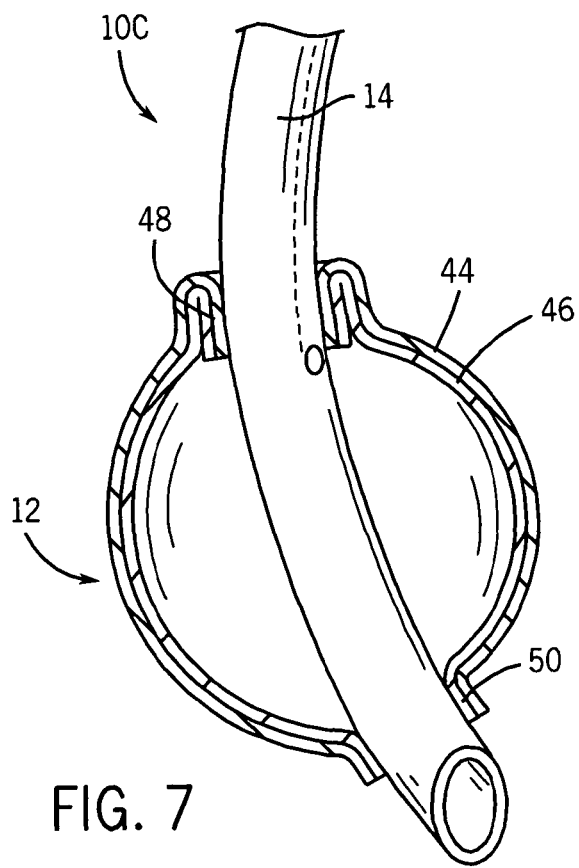
FIG. 6
FIG. 7

ENDOTRACHEAL CUFF AND TECHNIQUE FOR USING THE SAME

BACKGROUND OF THE INVENTION

1. Field of the Invention

The present invention relates to medical devices, and more particularly, to endotracheal devices, such as endotracheal tubes and cuffs.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to control the flow of air, food, fluids, or other substances into the patient. For example, medical devices such as tracheal tubes may be used to control the flow of one or more substances into or out of a patient. In many instances it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, tracheal tubes may be used to control the flow of air or other gases through a patient's trachea. Such tracheal tubes may include endotracheal (ET) tubes, tracheostomy tubes, or transtracheal tubes. To seal these types of tracheal tubes, an inflatable cuff may be associated with these tubes. When inflated, the cuff generally expands into the surrounding trachea to seal the tracheal passage around the open lumen of the tube.

As many patients are intubated for several days, healthcare workers may need to balance achieving a high-quality tracheal seal with possible patient discomfort. Typical cuffs may be divided into low pressure cuffs and high pressure cuffs on the basis of their respective intracuff pressures after cuff inflation. High pressure cuffs are typically made of highly elastic materials that may form a relatively smooth seal against the trachea. However, these highly elastic materials are relatively fragile, and may form tears or leaks. In order to overcome this disadvantage, these cuffs are typically manufactured with thicker walls. The thicker walls are in turn associated with higher inflation pressures, as lower pressures are insufficient to overcome the natural initial resistance of the cuff material to stretching. Thus, high pressure cuffs are often inflated to at least twice the intracuff pressure of lower pressure cuffs. Because higher cuff pressures are associated with patient discomfort, physicians are often reluctant to inflate such high pressure cuffs fully in order to achieve an optimal seal. The mechanical pressure of the cuff against the tracheal walls may also cause temporary damage to cilial structures in the trachea that are associated with airway particle clearance. Thus, cilial injury may result in a temporary decrease in a patient's ability to remove bacteria or other foreign particles from the trachea.

While low pressure cuffs may be used to avoid patient discomfort, these low pressure cuffs may be associated with a lower quality cuff seal against the trachea. Although low pressure cuffs are generally made from more robust materials that are less elastic than high pressure cuffs, such cuffs may not achieve the smooth sealing surface associated with high pressure cuffs. For example, low cuff inflation pressures may be associated with allowing folds to form in the walls of the low pressure cuff that may serve as leak paths for air as well as microbe-laden secretions. In order to fit a range of trachea anatomies with a given size of tracheal tube, cuff diameters of low pressure cuffs are usually about one and a half times the diameter of the average trachea. Therefore, when inserted in an average-sized trachea, such a cuff is unable to fully expand and will fold in on itself within the trachea. These folds may serve as leak paths that allow microbe laden secretions to flow past the cuff and enter the lung.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided an An inflatable balloon cuff for a medical device comprising:
an inner layer adapted to be coupled to a conduit; and an outer layer, wherein the outer layer is more elastic than the inner layer, and wherein the inner layer and the outer layer are substantially nonintegral with one other in at least a portion of the balloon cuff.

There is also provided a cuffed endotracheal tube that includes: a conduit; and an inflatable balloon cuff disposed on the conduit, the inflatable balloon cuff including: an inner layer; and an outer layer disposed proximate to the inner layer, wherein the outer layer is more elastic than the inner layer, and wherein the inner layer and the outer layer are substantially nonintegral with one other in at least a portion of the balloon cuff.

There is also provided a method of sealing a patient's trachea that includes: inserting an endotracheal tube having a double-layered inflatable cuff into a patient's trachea; inflating an inner layer of the double-layered cuff; and inflating an outer layer of the double-layered cuff.

There is also provided a method of manufacturing an inflatable balloon cuff that includes: providing a balloon cuff inner layer; and providing a balloon cuff outer layer disposed proximate to the inner layer, wherein the outer layer is more elastic than the inner layer, and wherein the inner layer and the outer layer are substantially nonintegral with one other in at least a portion of the balloon cuff.

There is also provided an inflatable balloon cuff for a medical device that includes: an inner layer adapted to be coupled to a conduit; and a relatively more elastic outer layer disposed proximate to the inner layer, wherein inflating the inner layer causes the outer layer to inflate.

There is also provided a low pressure inflatable balloon cuff for a medical device that includes: an inner layer adapted to be coupled to a conduit; and a relatively more elastic outer layer disposed proximate to the inner layer, wherein when the inner layer is inflated at low pressure, the outer layer forms a relatively smooth surface surrounding the inner layer.

BRIEF DESCRIPTION OF THE DRAWINGS

Advantages of the invention may become apparent upon reading the following detailed description and upon reference to the drawings in which:

FIG. 5 illustrates the uninflated multi-layer balloon cuff that forms a sheath around the endotracheal tube including in accordance with aspects of the present technique;

FIG. 6 illustrates an endotracheal tube with a separate lumen for inflation of each layer of the cuff;

FIG. 7 illustrates an endotracheal tube with a partially inflated multi-layer balloon cuff in which the two layers of the cuff are sealed over one another on the endotracheal tube;

DETAILED DESCRIPTION OF SPECIFIC EMBODIMENTS

Figure 1:
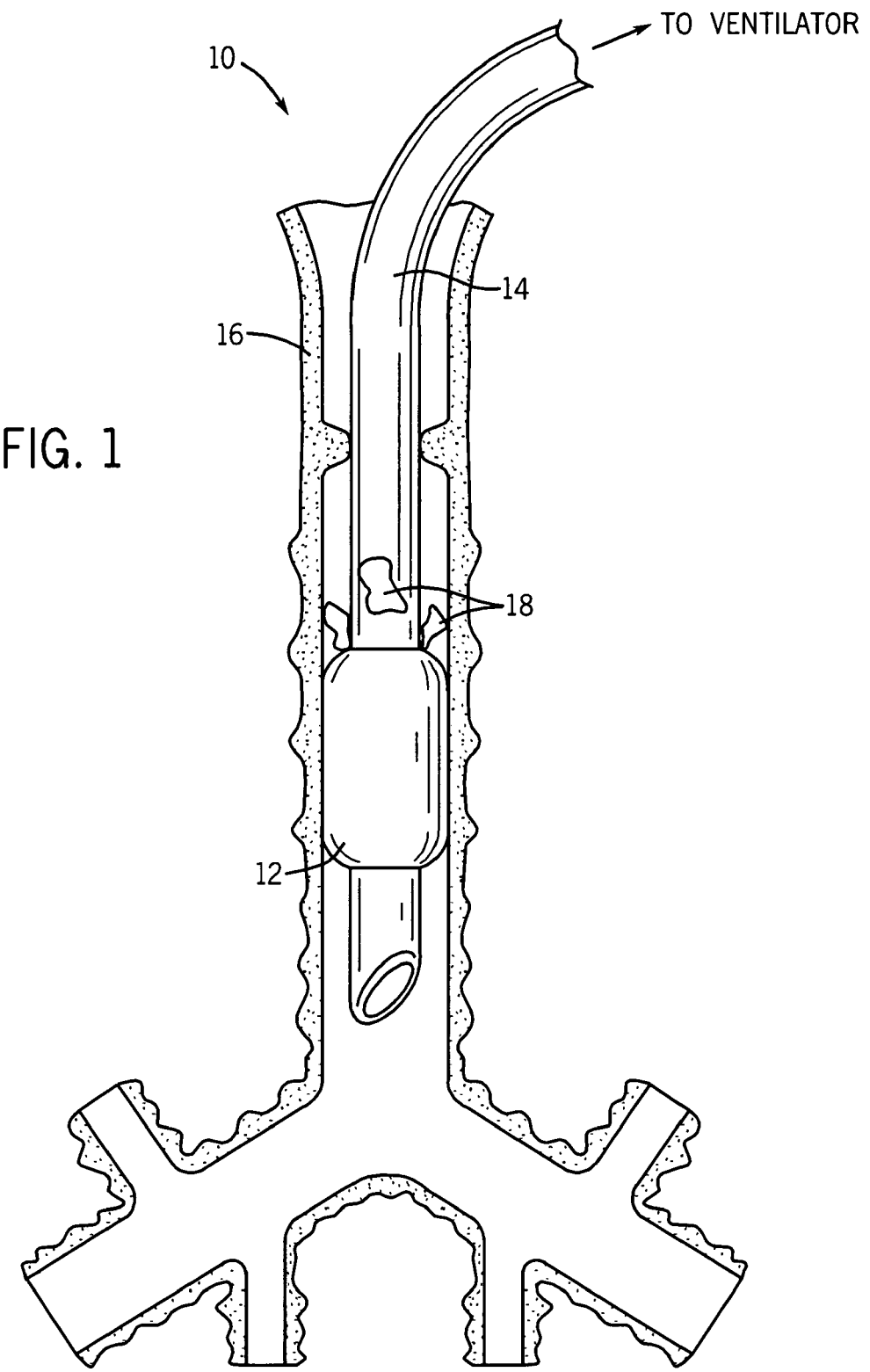
FIG. 1 illustrates a multi-layer balloon cuffed endotracheal tube of the present techniques that is inserted into a patient's trachea.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a medical balloon such as an endotracheal cuff or other medical device that may have an improved seal when inserted into a patient's trachea. In accordance with some aspects of the present technique, a multi-layer medical balloon is provided that is adapted to be used with an endotracheal tube or device. Such a device may be inserted into a patient's trachea to form an improved seal against a tracheal wall. The cuff includes at least two layers, with a tissue-contacting outer layer that is substantially more elastic than an inner layer of the cuff. The material properties of the outer layer may encourage the formation of a smooth surface when the cuff is inflated within a patient's trachea. Thus, while the inner layer may form small folds, the outer layer may serve to smooth over such folds, which may in turn reduce the number of leak paths formed in the cuff. Further, the multi-layer configuration of the cuff may serve as an improved barrier that reduces the outflow of gas from an inflated cuff and thus reduces leaks that deteriorate that quality of the cuff's seal over time. Also, such a barrier may prevent the inflow of anesthesia gases into a fully inflated cuff and may reduce cuff overinflation as well as any resulting patient discomfort.

The multi-layer inflatable balloon cuffs as provided herein combine the advantages of the comfort and structural stability of a low pressure cuff with the relatively smooth seal of a high pressure cuff. Endotracheal cuffs utilizing inflation pressures significantly greater than 25 cm $H_2O$, such as 50 cm $H_2O$, may be referred to as high-pressure cuffs, while cuffs that are designed to be inflated at pressures less than 25 cm $H_2O$ may be considered low-pressure cuffs. In order to compensate for the relatively fragile elastic material, a typical high pressure cuff uses thick cuff wall to avoid tears or leaks. The present cuffs include an inner layer that provides structure and support to the cuff, allowing a thinner elastic layer to be used as an outer cuff layer. The thickness of the elastic layer is related to the initial resistance of the material against stretching. The inflation curve of the cuff initially starts flat, as the interior cuff pressure increases without a change in volume. The interior pressure of the cuff reaches a certain pressure threshold, after which the elastic outer layer begins to stretch such that the volume of the cuff increases as more fluid enters the cuff, which allows the cuff to achieve its inflated state. A thinner outer layer is associated with a lower threshold for inflation. Accordingly, a thinner elastic layer may be inflated at the lower pressures associated with low pressure cuffs and may provide a relatively smooth seal at these low pressures. The multi-layer cuffs provide the advantage of reduced cuff wrinkling at low pressures, which may increase patient comfort while reducing microbial infiltration into the lungs.

Inflatable balloon cuffs as provided herein may be used in conjunction with any suitable medical device. In certain embodiments, the cuffs as provided herein may be used in conjunction with a catheter, a stent, a feeding tube, an intravenous tube, an endotracheal tube, a circuit, an airway accessory, a connector, an adapter, a filter, a humidifier, a nebulizer, or a prosthetic, in various embodiments.

An example of an inflatable cuff used in conjunction with a medical device is an endotracheal tube 10, depicted in FIG. 1. FIG. 1 shows an exemplary endotracheal tube 10 that has been inserted into a patient's trachea. The multi-layer cuff 12 is inflated to form a seal against the tracheal walls 16 and may prevent secretions 18 or other detritus from passing through the trachea into the lungs. The cuff 12 presents a relatively smooth surface to the tracheal walls 16, as the outer layer of the cuff smooths over any wrinkles formed by the inner layer, as discussed below.

The multi-layer cuff 12 includes at least two discrete layers that are nonintegral with one another. These layers are not adhesively bonded to one another in at least part of the inflatable region of the cuff. (As provided in certain embodiments discussed below, the inner layer and the outer layer may be joined to one another where they are attached to the conduit 14.) Such a configuration allows an outer elastic layer to stretch smoothly over an inner support layer as the inner layer inflates. Because the outer layer is not bonded or otherwise adhesively attached to the inner layer, the outer layer may not conform to any wrinkles that form in the less elastic inner layer, but may instead form a smooth surface over the inner layer.

Figure 2:
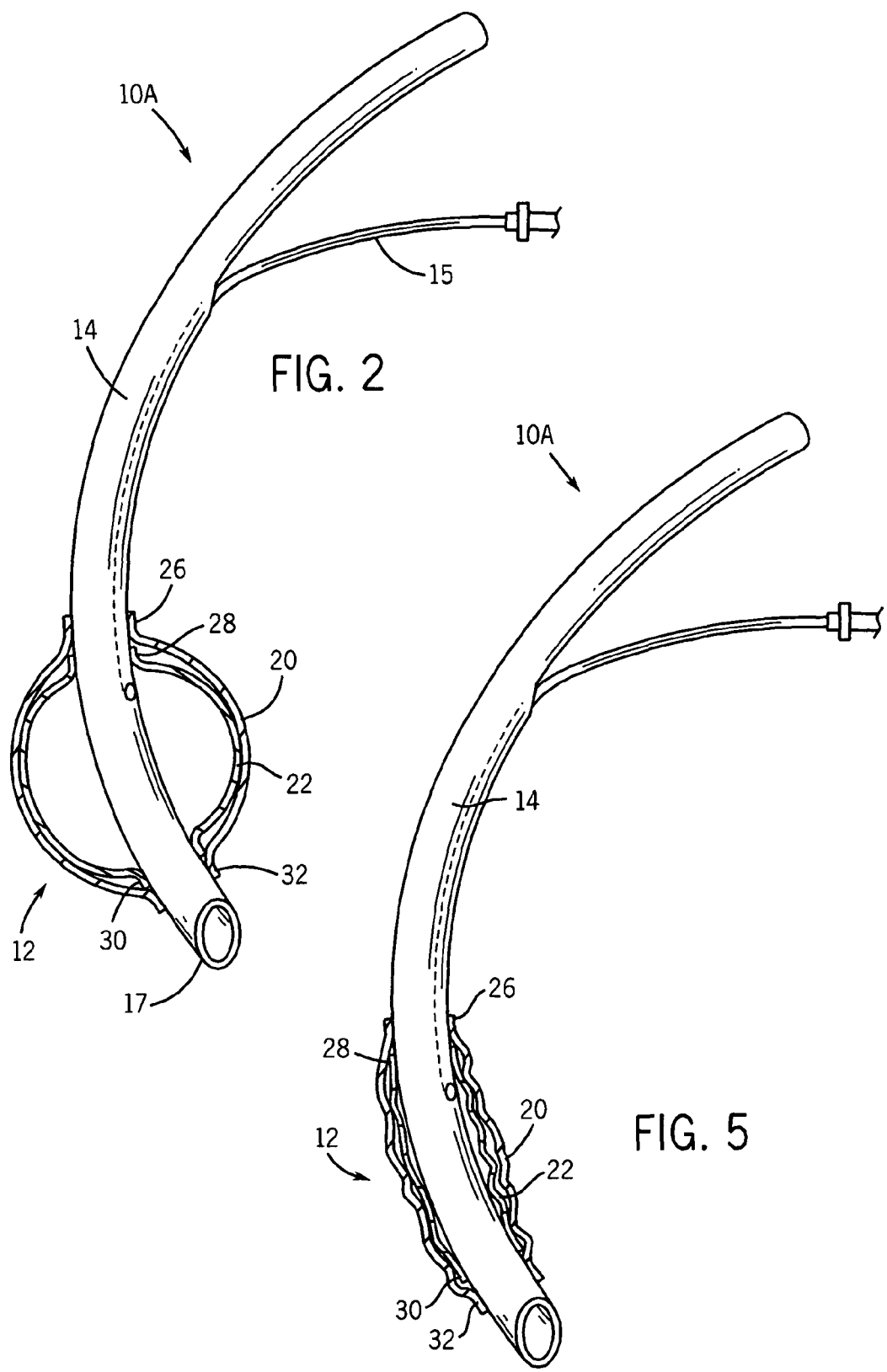
FIG. 2 illustrates an endotracheal tube with an inflated multi-layer balloon cuff including in accordance with aspects of the present technique.

As shown in FIG. 2, an exemplary endotracheal tube 10a includes a multi-layer cuff 12. The cuff 12 has an inner layer 20 and an outer layer 22. The outer layer 22 and the inner layer 20 may be adhesively or otherwise bonded to the conduit 14. As shown, the inner layer has a proximal adhesion point 28 and a distal adhesion point 30, while the outer layer has a proximal adhesion point 26 and a distal adhesion point 32. While these adhesion points are depicted in FIG. 2 as non-overlapping, in other embodiments, one or more of the cuff adhesion points may overlap with one another. Generally, the inner layer 20 and/or the outer layer 22 may be bonded to the conduit 14 by any suitable method, such as heat sealing or with adhesives. In specific embodiments, the outer layer 22 may be adhered to the conduit 14 with a dilute cyanoacrylate adhesive or a UV cure adhesive. The cuff 12 is disposed on a conduit 14 that is suitably sized and shaped to be inserted into a patient and allow the passage of air through the conduit 14. Typically, the cuff 12 is disposed, adhesively or otherwise, towards the distal end 17 of the conduit 14. The cuff 12 may inflated and deflated via a lumen 15 in communication with the cuff 12. The cuff 12 depicted in FIG. 2 is in an inflated state. Generally, when fluid passes through the lumen 15, the multi-layer cuff 12 is inflated by the increased pressure that inflates the inner layer 20, which in turn applies pressure to and inflates the outer layer 22.

The inner layer 20 may be formed from materials having suitable mechanical properties (such as puncture resistance, pin hole resistance, tensile strength), chemical properties (such as forming a suitable bond to the conduit 14, and biocompatibility. In one embodiment, the walls of the inner layer 20 are made of a polyurethane having suitable mechanical and chemical properties. An example of a suitable polyurethane is Dow Pellethane® 2363-80A. In another embodiment, the walls of the inner layer are made of a suitable polyvinyl chloride (PVC). In some embodiments, the walls of the inner layer 20 may be 0.0003 inches-0.0025 inches thick. In certain embodiments, a relatively thin (e.g. less than 0.0003 inches thick) inner layer 20 may be employed as the outer layer 22 may provide additional structural support to the cuff 12. The inner layer 20 may be generally sized and shaped like a typical high volume, low pressure cuff.

The outer layer 22 may be any suitable elastic material that is relatively more elastic than the inner layer 20. For example, the outer layer may be latex, rubber, silicone, neoprene, nitrile, or polyisoprene. In one embodiment, the outer layer is a polyisoprene and is 0.0002 inches thick with tensile strength of 2500-4000 psi and with an elongation at break of 300-800%. In certain embodiments, the outer layer 22 may be able to be elongated more than 300% before break, or more than 500% before break. Polyisoprene may be more advantageous than latex, as certain patients may have latex allergies. In certain embodiments, the outer layer 22 may include antioxidant material compounded into material of the outer layer 22 for added strength. The outer layer 22 may be any elastic material of suitable thickness that is capable of being inflated to seal the trachea at pressures of less than 50 cm $H_2O$ or, in a specific embodiment, less than 25 cm $H_2O$. For example, the outer layer may be less than 0.0025 inches thick, and may be 0.0005 inches in thickness. The outer layer 22 may be generally sized and shaped to conform to the size and shape of the conduit 14. For example, the outer layer 22 may be approximately 10 mm or less in diameter in an unbiased state. Further, the outer layer 22 may be 50 mm or less in length along the conduit 14 in an unbiased state. Generally, the outer layer 22 may be substantially tube-shaped in the unbiased state, or may have a slight barrel shape.

The inner layer 20 or the outer layer 22 may be manufactured by any suitable method, including extrusion, co-extrusion, spraying, dipping, coating, or deposition. For example, an inner layer 20 or an outer layer 22 as provided herein may be manufactured by an extrusion process. For example, the inner layer 20 or outer layer 22 may be made by using extruded or pre-extruded tubing and applying heat and pressure appropriately within a molding cavity to achieve the desired shape (blow molding). The inner layer 20 or outer layer 22 can also be formed by extrusion blow molding, wherein an extruder fed polymer pellets melts the polymer and feeds the molten polymer through a die to form a tube shape. This still molten polymer is then captured in a mold and air pressure is applied to expand the tube out to the walls of the mold, thus achieving the desired shape. In the extrusion blow molding process, a core or mandrel of the extruder has apertures to admit a gas such as pressurized air or an inert gas like nitrogen, into the medical device in the neighborhood of the cuff. After a length of medical device has been extruded, a mold clamps the medical device around the mandrel. As gas is admitted to the cuff area through the mandrel, the cuff expands against the mold. In the alternative, the cuff wall may be expanded in a second discrete expansion process following an extrusion or molding process, such as with a shuttle blow molding process. After initial extrusion, the extruded inner layer 20 will have a generally tubular shape with a substantially uniform wall thickness. This tubular shape may then be blown into the tapered shape. This process results in the area of the cuff with larger diameters having thinner walls because the same amount of material is stretched over a larger area. A programmable parison allows the wall thickness being extruded to be controlled as a function of length.

Figure 3:
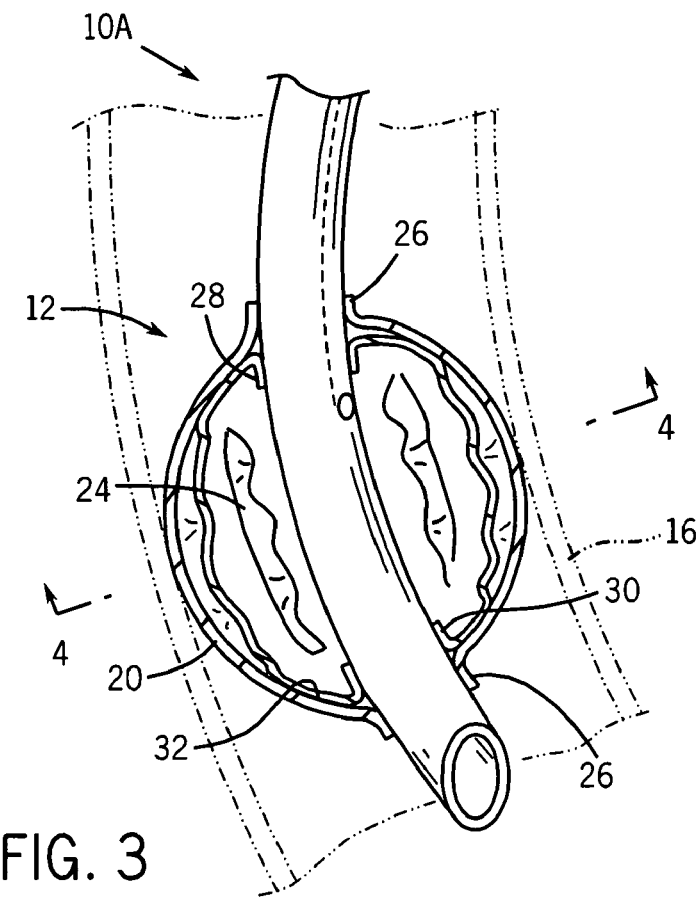
FIG. 3 illustrates the inner wrinkled layer and outer smooth layer of the multi-layer balloon cuff in a patient's trachea.
Figure 4:
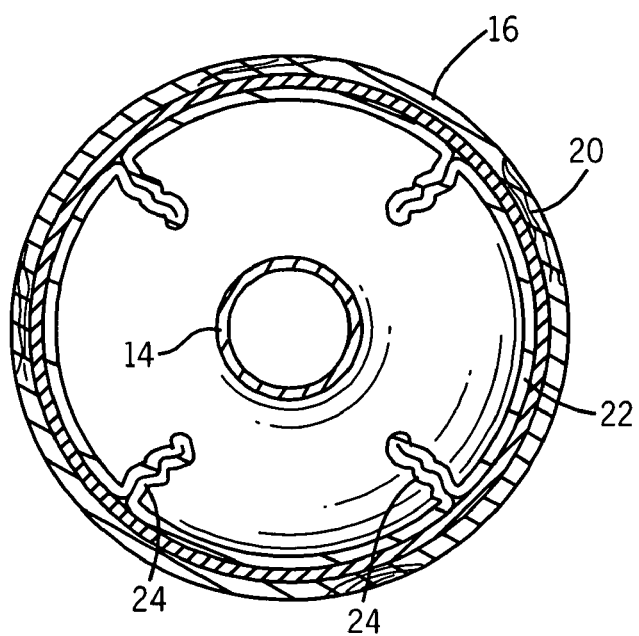
FIG. 4 is a cross-sectional view of the endotracheal tube of FIG. 3.

As shown in FIG. 3, the endotracheal tube 10a may be inserted into a patient's trachea to form a smooth seal against the tracheal walls 16. The inner layer 20 may be adapted such that the diameter of the fully inflated inner layer is larger than the size of the tracheal passage. As the inner layer 20 inflates, the inner layer 20 may increase in volume until its fully inflated volume is realized. However, when the cuff 12 is inserted into a patient's trachea and inflated, the inner layer 20 is unable to inflate to its maximum diameter and the walls of the inner layer 20 may fold in on themselves in order to fit in the trachea, which causes wrinkles 24 and leak paths to form. The inner layer 20 may be inflated within a patient's trachea such that the intra cuff pressure is approximately 20-25 cm $H_2O$. Because the outer layer 22 is significantly more elastic than the inner layer 20, its material properties result in a less wrinkled, relatively smooth interface with the tracheal walls 16. The inflation of the inner layer 20 may exert pressure on the more elastic outer layer 22, which may respond to the increase in pressure by stretching its walls to expand in size. During this period of elastic stretching of the outer layer 22, the outer layer 22 is substantially smooth and unwrinkled. FIG. 4 is a cross-section of a cuff 12 that has been inserted into a patient's trachea and inflated to form a seal against the tracheal walls 16. The outer layer 22 is shown to smooth over the wrinkles 24 formed in the inner layer 20, forming a smooth sealing surface against the tracheal walls 16, which may reduce or eliminate leak paths that may allow mucosal secretions to flow into the lungs.

As shown in FIG. 5, the outer layer 22 may be applied over the inner layer 20 such that it exerts an elastic pressure on the inner layer 20. Therefore, the dimensions of the outer layer 22 may be slightly smaller than those of the inner layer 20, such that the outer layer 22 is stretched over the inner layer 20. Thus, in the uninflated state, the outer layer 22 may be at least slightly elastically biased. For example, the outer layer 22 may be stretched to at least 120% or at least 200% of its unbiased size. Accordingly, the outer layer 22 may exert elastic pressure on the inner layer 20 to push the inner layer 20 towards the conduit 14, which may serve to minimize the cross-sectional profile of the endotracheal tube 10. The outer layer 22 may generally be smooth against the conduit 14, except where the wrinkled inner layer 20 may cause the outer layer to display bumps on its uninflated surface. Such an embodiment may be advantageous because biasing the outer layer 22 may facilitate its stretching as the inner layer 20 exerts pressure on it. This may also provide the advantage of allowing easier insertion of the endotracheal tube 10, as in such an embodiment, the cuff 12 may be only slightly larger in diameter than the conduit 14. This may not only provide a more comfortable insertion for the patient, as the cuff 12 may be relatively smaller than a typical cuff, but the tight fit against the conduit 14 may also reduce the possibility of a cuff 12 snagging or tearing on a patient's teeth while being inserted through the mouth.

FIG. 6 illustrates an endotracheal tube 10b with separate lumen for inflation of the outer layer 38 and the inner layer 40. The inner layer 40 may be inflated by a lumen 34 while the outer layer 38 may be inflated by a lumen 36. In such an embodiment, the inner layer adhesion points 43 and 45 are nonoverlapping with the outer layer adhesion points 41 and 42 in order to create a closed space between the inner layer 40 and the outer layer 38. While typical cuffs are inflated with air, any fluid may be used to inflate the inner layer 40 or the outer layer 38.

Alternatively, it may be advantageous to provide an endotracheal tube 10 in which the inner layer and the outer layer adhere to the conduit at overlapping points. FIG. 7 illustrates an endotracheal tube 10c in which the outer layer 44 and the inner layer 46 are sealed over one another on the conduit 14. The outer layer 44 may exert elastic pressure on the inner layer 46 at the adhesion points 48 and 50, which may further strength the seal to the conduit 14. Such a configuration may also provide certain manufacturing advantages, because the number of adhesion points to the conduit 14 is minimized.

Figure 8:
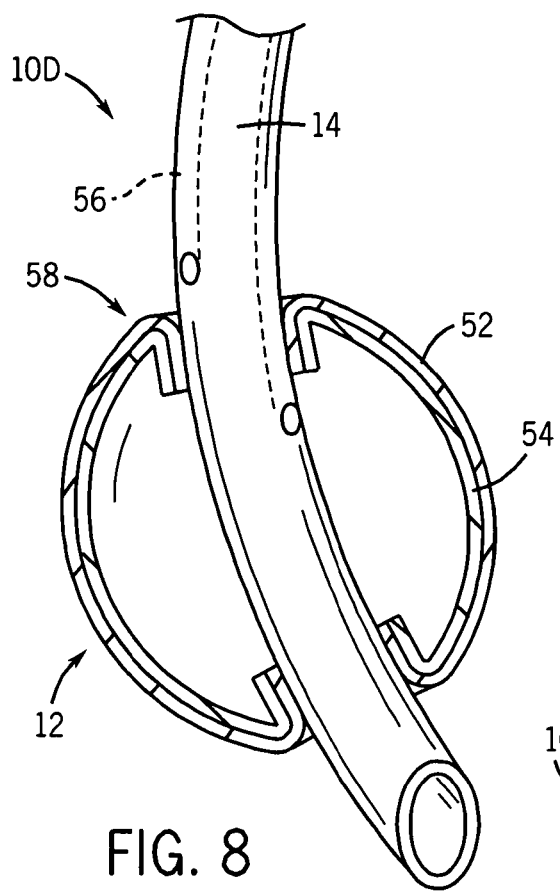
FIG. 8 illustrates an endotracheal tube with a fully inverted shoulder seal on the endotracheal tube.
Figure 9:
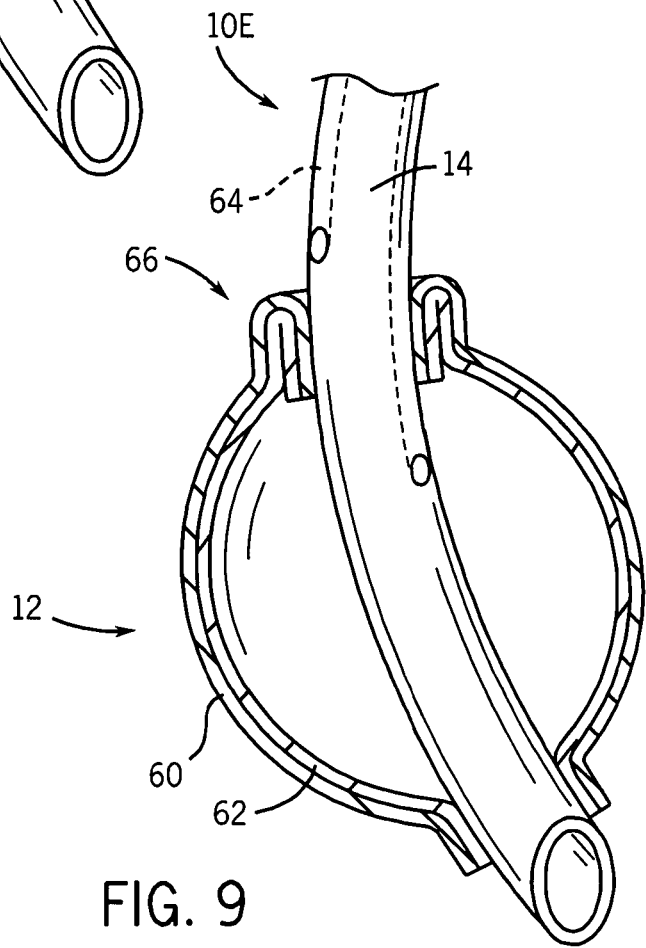
FIG. 9 illustrates an endotracheal tube with a half-inverted shoulder seal on the endotracheal tube.
Figure 3:
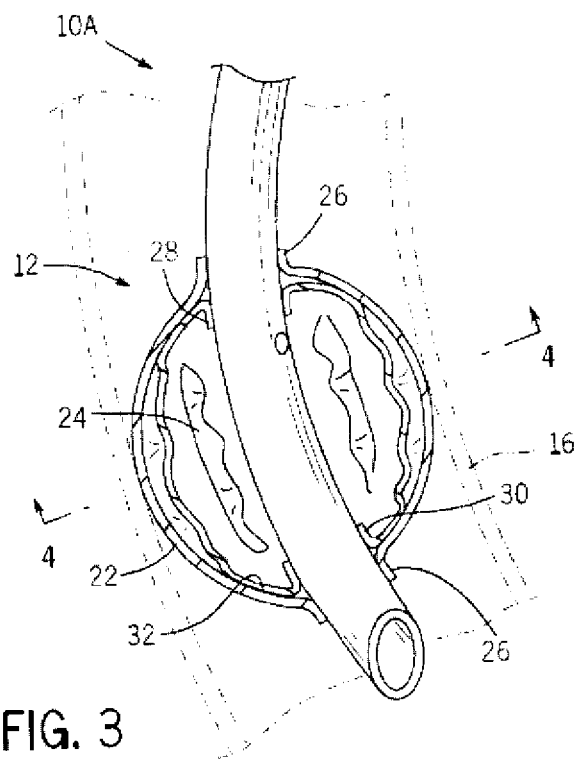
Figure 4:
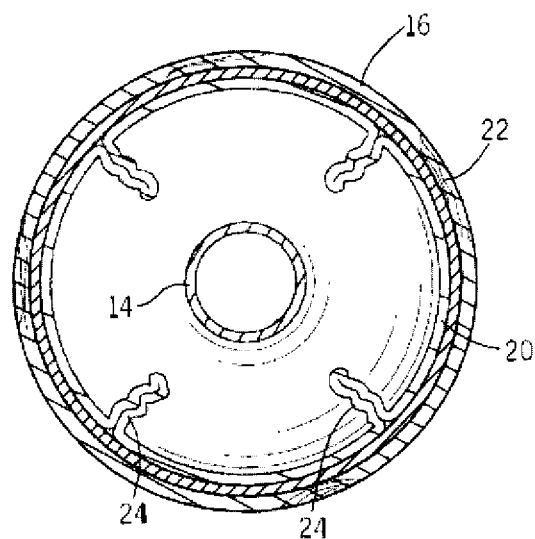

The multi-layer cuffs 12 may also be sealed to the tube 14 in a configuration adapted to facilitate aspiration of any secretions that may build up on the surface of the cuff 12. FIG. 8 illustrates an endotracheal tube 10d with a fully inverted shoulder seal. In a fully inverted shoulder seal, the inner layer 54 and the outer layer 52 are folded over one another and tucked against the conduit 14 such that the outer layer 52 contacts the conduit 14. This changes the placement of the cuff adhesion points from the exterior of the cuff 12 to the interior of the cuff 12, which results in the region of the conduit 14 nearest top 58 of the cuff 12 being free of adhesion points. This configuration provides the advantage of allowing an aspiration lumen 56 to be placed very close to area 58 at the top of the cuff 12, where secretions may tend to build up. This may lead to more efficient aspiration of mucosal secretions, which may reduce microbial infiltration into the lungs. FIG. 9 illustrates an alternative endotracheal tube 10e with a half-inverted shoulder seal on the conduit 14. In this embodiment, the outer layer 60 is folded over the inner layer 62, but the adhesion point is on the exterior of the cuff 12. Further, the shoulder seal is only placed at the top 66 of the cuff 12. As the shoulder seal configuration is relatively challenging from a manufacturing standpoint, it may be advantageous to only have a single shoulder seal placed at the area at the top 66 of the cuff 12 nearest the aspiration lumen 64.

The tracheal cuffs 12 of the present techniques may be incorporated into systems that facilitate positive pressure ventilation of a patient, such as a ventilator. Such systems may typically include connective tubing, a gas source, a monitor, and/or a controller. The controller may be a digital controller, a computer, an electromechanical programmable controller, or any other control system.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

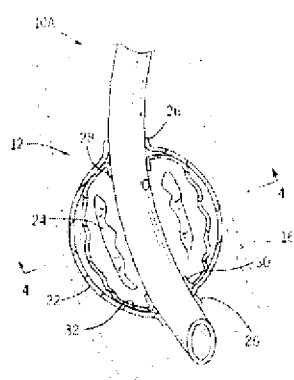 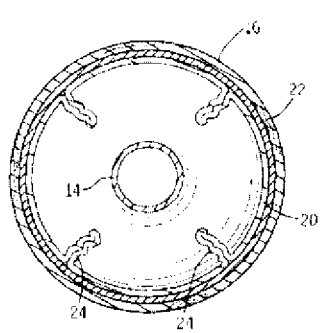

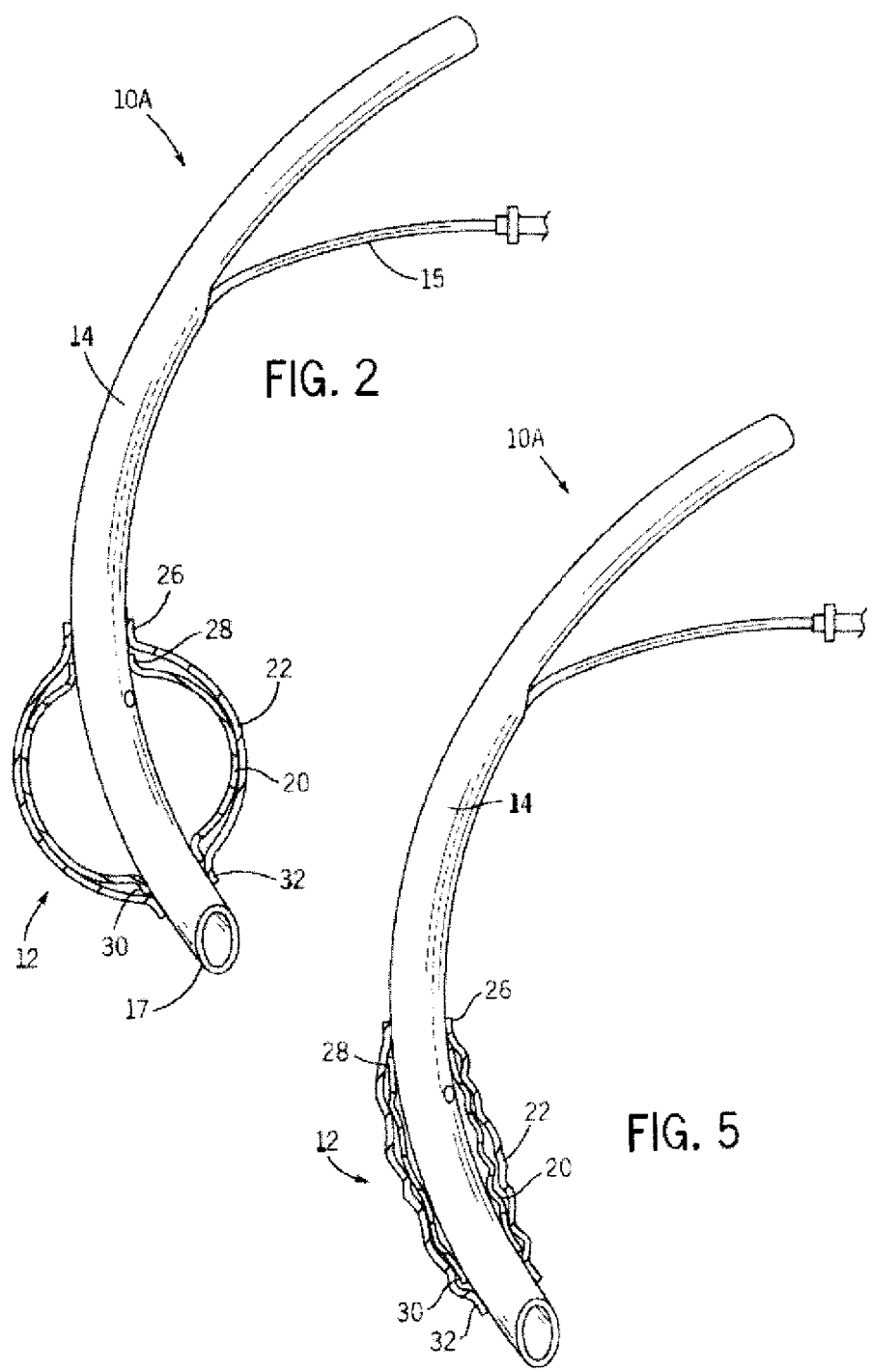

What is claimed is:

1. A medical device comprising:
a conduit configured to deliver gas to a patient's trachea; and
a balloon cuff comprising:
an inner layer adapted to be coupled to the conduit; and
an outer layer disposed proximate to the inner layer, wherein the outer layer is more elastic than the inner layer, and wherein the inner layer and the outer layer are substantially nonintegral with one another in at least a portion of the balloon cuff, and wherein the inner layer is configured to wrinkle when the balloon cuff is inflated within the patient's trachea.

2. The medical device of claim 1, wherein the inner layer comprises a material that is able to be elongated less than 200% of its length before break.

3. The medical device of claim 1, wherein the inner layer comprises polyethylene teraphthalate (PETP), low-density polyethylene (LDPE), polyvinyl chloride (PVC), silicone, neoprene, polyisoprene, or polyurethane (PU).

4. The medical device of claim 1, wherein the inner layer is less than 0.0025 inches in thickness.

5. The medical device of claim 1, wherein the inner layer is less than 0.0003 inches in thickness.

6. The medical device of claim 1, wherein the outer layer comprises a material that is able to be elongated at least 500% of its length before break.

7. The medical device of claim 1, wherein the outer layer comprises rubber, silicone, latex, or synthetic polyisoprene.

8. The medical device of claim 1, wherein the outer layer is less than 0.0025 inches in thickness.

9. The medical device of claim 1, wherein the outer layer is less than 0.0003 inches in thickness.

10. The medical device of claim 1, wherein the inner layer is adapted to be inflated at a pressure of 25 cm $H_2O$ or less.

11. The medical device of claim 1, wherein the inner layer is adapted to be inflated at a pressure of less than 15 cm $H_2O$.

12. The medical device of claim 1, wherein the outer layer is adapted to be inflated at a pressure of 25 cm $H_2O$ or less.

13. The medical device of claim 1, wherein the outer layer is adapted to be inflated at a pressure of 50 cm $H_2O$ or less.

14. The medical device of claim 1, wherein the conduit comprises an endotracheal tube.

15. The medical device of claim 1, wherein the conduit comprises a tracheostomy tube.

16. A cuffed endotracheal tube comprising:
a conduit defining a ventilation lumen; and
an inflatable balloon cuff disposed on the conduit, the inflatable balloon cuff comprising:
an inner layer; and
an outer layer disposed proximate to the inner layer, wherein the outer layer is more elastic than the inner layer, and wherein the inner layer and the outer layer are substantially nonintegral with one another in at least a portion of the balloon cuff, and wherein the inner layer is configured to wrinkle when the balloon cuff is inflated within the patient's trachea.

17. The cuffed endotracheal tube of claim 16, wherein the inner layer comprises a material that is able to be elongated less than 200% of its length before break.

18. The cuffed endotracheal tube of claim 16, wherein the inner layer comprises polyethylene teraphthalate (PETP), low-density polyethylene (LDPE), polyvinyl chloride (PVC), silicone, neoprene, polyisoprene, or polyurethane (PU).

19. The cuffed endotracheal tube of claim 16, wherein the outer layer comprises a material that is able to be elongated at least 500% of its length before break.

20. The cuffed endotracheal tube of claim 16, wherein the outer layer comprises rubber, silicone, latex, or synthetic polyisoprene.

21. The cuffed endotracheal tube of claim 16, wherein the inner layer is adapted to be inflated at a pressure of 25 cm $H_2O$ or less.

22. The cuffed endotracheal tube of claim 16, wherein the inner layer is adapted to be inflated at a pressure of less than 15 cm $H_2O$.

23. The cuffed endotracheal tube of claim 16, wherein the outer layer is adapted to be inflated at a pressure of 25 cm $H_2O$ or less.

24. The cuffed endotracheal tube of claim 16, wherein the outer layer is adapted to be inflated at a pressure of 50 cm $H_2O$ or less.

25. The cuffed endotracheal tube of claim 16, wherein the inner layer is less than 0.0025 inches in thickness.

26. The cuffed endotracheal tube of claim 16, wherein the inner layer is less than 0.0003 inches in thickness.

27. The cuffed endotracheal tube of claim 16, wherein the outer layer is less than 0.0025 inches in thickness.

28. The cuffed endotracheal tube of claim 16, wherein the outer layer is less than 0.0003 inches in thickness.

29. The cuffed endotracheal tube of claim 16, comprising an inflation lumen disposed on the conduit that is adapted to inflate the inner layer.

30. The cuffed endotracheal tube of claim 16, comprising an inflation lumen disposed on the conduit that is adapted to inflate the outer layer without inflating the inner layer.

31. The cuffed endotracheal tube of claim 16, wherein the endotracheal tube is operatively connected to a ventilator.

32. A method of sealing a patient's trachea comprising:
inserting an endotracheal tube having a double-layered inflatable cuff into a patient's trachea; and
inflating an inner layer of the double-layered cuff, wherein inflating the inner layer causes expansion of an outer layer of the double-layered cuff, wherein the outer layer is more elastic than the inner layer, and wherein the inner layer is configured to wrinkle when the balloon cuff is inflated within the patient's trachea.

33. A method of manufacturing a medical device, comprising:
providing an inner layer of a balloon cuff; and
providing an outer layer of the balloon cuff disposed proximate to the inner layer, wherein the outer layer is more elastic than the inner layer, and wherein the inner layer and the outer layer are substantially nonintegral with one another in at least a portion of the balloon cuff, and wherein the inner layer is configured to wrinkle when the balloon cuff is inflated within the patient's trachea; and
disposing the balloon cuff on a tracheal tube.

34. The method of claim 33, wherein providing the inner layer comprises providing a material that is able to be elongated less than 200% of its length before break.

35. The method of claim 33, wherein providing the inner layer comprises providing an inner layer comprising polyethylene teraphthalate (PETP), low-density polyethylene (LDPE), polyvinyl chloride (PVC), silicone, neoprene, polyisoprene, or polyurethane (PU).

36. The method of claim 33, wherein providing the outer layer comprises providing a material that is able to be elongated at least 500% of its length before break.

37. The method of claim 33, wherein providing the outer layer comprises providing an outer layer comprising rubber, silicone, latex, or synthetic polyisoprene.

38. The method of claim 33, wherein providing the inner layer comprises providing an inner layer adapted to be inflated at a pressure of 25 cm $H_2O$ or less.

39. The method of claim 33, wherein providing the inner layer comprises providing an inner layer adapted to be inflated at a pressure of less than 15 cm $H_2O$.

40. The method of claim 33, wherein providing the outer layer comprises providing an outer layer to be inflated at a pressure of 25 cm $H_2O$ or less.

41. The method of claim 33, wherein providing the outer layer comprises providing an outer layer adapted to be inflated at a pressure of 50 cm $H_2O$ or less.

42. The method of claim 33, wherein providing the inner layer comprises providing an inner layer less than 0.0025 inches in thickness.

43. The method of claim 33, wherein providing the inner layer comprises providing an inner layer less than 0.0003 inches in thickness.

44. The method of claim 33, wherein providing the outer layer comprises providing an outer layer less than 0.0025 inches in thickness.

45. The method of claim 33, wherein providing the outer layer comprises providing an outer layer less than 0.0003 inches in thickness.

46. An inflatable balloon cuff for a medical device comprising:
an inner layer adapted to be coupled to a tracheal tube; and
a relatively more elastic outer layer disposed proximate to the inner layer, wherein inflating the inner layer causes the outer layer to inflate, and wherein the inner layer is configured to wrinkle when the balloon cuff is inflated within the patient's trachea.

47. A low pressure inflatable balloon cuff for a medical device comprising:
an inner layer adapted to be coupled to tracheal tube; and
a relatively more elastic outer layer disposed proximate to the inner layer, wherein when the inner layer is inflated at low pressure, the outer layer forms a relatively smooth surface surrounding the inner layer, and wherein the inner layer is configured to wrinkle when the balloon cuff is inflated within the patient's trachea.

48. A medical device comprising:
an inflatable balloon cuff disposed on a tracheal tube, the inflatable balloon cuff comprising:
an inner layer coupled to the tracheal tube; and
an outer layer disposed proximate to the inner layer, wherein the outer layer is more elastic than the inner layer, and wherein the inner layer and the outer layer are substantially nonintegral with one another in at least a portion of the balloon cuff, and wherein the inner layer is configured to wrinkle when the balloon cuff is inflated within the patient's trachea; and
a single inflation lumen disposed on or in the tracheal tube comprising an opening in fluid communication only with the interior of the inner layer.

49. A medical device comprising:
an inflatable balloon cuff disposed on a tracheal tube, the inflatable balloon cuff comprising:
an inner layer coupled to the tracheal tube; and
an outer layer disposed proximate to the inner layer, wherein the outer layer is more elastic than the inner layer, and wherein a majority of an exterior surface of the inner layer is in contact with the outer layer when the inner layer is inflated, and wherein the inner layer is configured to wrinkle when the balloon cuff is inflated within the patient's trachea.

50. A medical device comprising:
an inflatable balloon cuff disposed on a tracheal tube, the inflatable balloon cuff comprising:
an inner layer coupled to the tracheal tube; and
an outer layer disposed proximate to the inner layer, wherein the outer layer is more elastic than the inner layer, and wherein the inner layer has a larger surface area than the outer layer, and wherein the inner layer is configured to wrinkle when the balloon cuff is inflated within the patient's trachea.

* * * * *

UNITED STATES PATENT AND TRADEMARK OFFICE
CERTIFICATE OF CORRECTION

PATENT NO. : 8,307,830 B2  
APPLICATION NO. : 11/540354  
DATED : November 13, 2012  
INVENTOR(S) : Jessica Clayton It is certified that error appears in the above-identified patent and that said Letters Patent is hereby corrected as shown below:

Delete the title page and substitute therefore with the attached title page consisting of the corrected illustrative figure.

In the Drawings

Delete Drawing Sheets 2 and 3 and substitute therefore with the attached Drawing Sheets 2 and 3 consisting of replacement FIGS. 2-5.

Signed and Sealed this  
Twenty-sixth Day of August, 2014

Michelle K. Lee  
*Deputy Director of the United States Patent and Trademark Office*

United States Patent
Clayton

(10) Patent No.: US 8,307,830 B2
(45) Date of Patent: Nov. 13, 2012

(54) ENDOTRACHEAL CUFF AND TECHNIQUE FOR USING THE SAME

(75) Inventor: Jessica Clayton, Campbell, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1784 days.

(21) Appl. No.: 11/540,354

(22) Filed: Sep. 29, 2006

(65) Prior Publication Data

US 2008/0078403 A1 Apr. 3, 2008

(51) Int. Cl.
  *A61M 16/00* (2006.01)
  *A61M 29/00* (2006.01)
  *A61M 31/00* (2006.01)
  *A61F 2/06* (2006.01)

(52) U.S. Cl. ........ 128/207.15; 128/200.26; 128/207.14; 128/207.16; 604/101.02; 604/101.05; 604/103.05; 604/103.06; 604/103.11; 604/103.12; 604/103.13; 604/103.14; 604/500; 604/509; 606/191; 606/192; 606/193; 606/194; 623/1.11

(58) Field of Classification Search ............ 128/200.26, 128/207.14, 207.15, 207.16; 604/101.02, 604/500, 509, 101.05, 103.05, 103.06, 103.11, 604/103.12, 103.13, 103.14; 606/193, 191, 606/192, 194; 623/1.11

See application file for complete search history.

(56) References Cited

U.S. PATENT DOCUMENTS

| | | | |
|---|---|---|---|
| 2,927,584 A | 3/1960 | Wallace | |
| 3,769,983 A | 11/1973 | Merav | |
| 3,810,474 A | 5/1974 | Cross | |
| 3,822,238 A | 7/1974 | Blair et al. | |
| 3,913,565 A | 10/1975 | Kawahara | |
| 3,971,385 A | 7/1976 | Corbett | |
| 3,975,350 A | 8/1976 | Hudgin et al. | |
| 3,995,643 A | 12/1976 | Merav | |
| 4,022,217 A | 5/1977 | Rowean | |
| 4,130,617 A | 12/1978 | Wallace | |
| 4,230,108 A | 10/1980 | Young | |
| 4,231,365 A | 11/1980 | Scarberry | |
| 4,235,239 A | 11/1980 | Elam | |
| 4,328,056 A * | 5/1982 | Snooks | 156/242 |
| 4,340,046 A | 7/1982 | Cox | |
| 4,417,576 A | 11/1983 | Baran | |
| 4,495,948 A | 1/1985 | Shapiro | |
| 4,552,558 A | 11/1985 | Muto | |
| 4,569,344 A | 2/1986 | Palmer | |
| 4,638,539 A | 1/1987 | Palmer | |
| 4,649,913 A | 3/1987 | Watson | |

(Continued)

FOREIGN PATENT DOCUMENTS

CA 2353007 6/2000

(Continued)

OTHER PUBLICATIONS

International Search Report PCT/US2007/020543, 5 pages, mailed Nov. 27, 2008.

(Continued)

*Primary Examiner* — Patricia Bianco
*Assistant Examiner* — Nihir Patel

(57) ABSTRACT

A multi-layer inflatable balloon cuff may be adapted to seal a patient's trachea when associated with an endotracheal tube. The outer layer and the inner layer of the balloon cuff may have different material properties that may enhance a cuff's mechanical pressure seal by reducing wrinkles or folds that may form against a patient's tracheal walls.

50 Claims, 5 Drawing Sheets